(12) United States Patent
Weingartner et al.

(10) Patent No.: US 11,635,417 B2
(45) Date of Patent: Apr. 25, 2023

(54) DEVICE FOR DETECTING THE QUALITY OF A LIQUID IN A SUPPLY PIPE

(71) Applicant: SCAN MESSTECHNIK GESELLSCHAFT MBH, Vienna (AT)

(72) Inventors: Andreas Weingartner, Korneuburg (AT); Michael Lindner, Vienna (AT); Roman Morawek, Vienna (AT); Bernd Spigaht, Loerrach (DE)

(73) Assignee: SCAN MESSTECHNIK GESELLSCHAFT MBH, Vienna (AT)

( * ) Notice: Subject to any disclaimer, the term of this patent is extended or adjusted under 35 U.S.C. 154(b) by 431 days.

(21) Appl. No.: 16/650,294

(22) PCT Filed: Sep. 20, 2018

(86) PCT No.: PCT/AT2018/060219
§ 371 (c)(1),
(2) Date: Mar. 24, 2020

(87) PCT Pub. No.: WO2019/056036
PCT Pub. Date: Mar. 28, 2019

(65) Prior Publication Data
US 2020/0225205 A1 Jul. 16, 2020

(30) Foreign Application Priority Data
Sep. 25, 2017 (AT) .............................. A 50814/2017

(51) Int. Cl.
*G01N 33/18* (2006.01)
*G01N 1/14* (2006.01)
*G01N 1/40* (2006.01)

(52) U.S. Cl.
CPC ........... *G01N 33/1893* (2013.01); *G01N 1/14* (2013.01); *G01N 2001/4088* (2013.01)

(58) Field of Classification Search
CPC .............. G01N 33/18; G01N 33/1806; G01N 33/1813; G01N 33/1826; G01N 33/182; G01N 33/1853; G01N 33/1893
See application file for complete search history.

(56) References Cited

U.S. PATENT DOCUMENTS 3,880,011 A * 4/1975 Johnson ................... G01N 1/14
73/864.35
4,014,216 A * 3/1977 Thornton ............. G01N 1/2247
73/863.61
(Continued)

FOREIGN PATENT DOCUMENTS

CA 1155683 A 10/1983
CA 2352999 A1 1/2002
(Continued)

OTHER PUBLICATIONS

ESPACENET Machine Translation of FR 2708347 A1 Which Originally Published on Feb. 3, 1995. (Year: 1995).*
(Continued)

*Primary Examiner* — David A. Rogers
(74) *Attorney, Agent, or Firm* — McCoy Russell LLP

(57) ABSTRACT

The invention relates to a device for detecting the quality of a liquid in a supply pipe, in particular for detecting the water quality in a water pipe, comprising a flow cell, which has an inlet opening, an outlet opening and at least one receiving device for the arrangement of at least one sensor. The inlet opening and the outlet opening are provided on a base surface of the flow cell intended for connection to the supply pipe, the inlet opening of the flow cell is connected to an intake pipe, the free end of which is intended for arrangement in the supply pipe, said intake pipe being received displaceably in its longitudinal direction in the flow cell or (Continued)

having an adjustable length, and a liquid pump of a flow of the liquid in the supply pipe is connected to the intake pipe.

20 Claims, 5 Drawing Sheets

(56) References Cited

U.S. PATENT DOCUMENTS

| | | | | |
|---|---|---|---|---|
| 4,307,620 | A * | 12/1981 | Jiskoot | G01N 1/2035 |
| | | | | 73/863.61 |
| 4,346,611 | A * | 8/1982 | Welker | G01N 1/2035 |
| | | | | 73/866.5 |
| 4,631,967 | A * | 12/1986 | Welker | G01L 19/0007 |
| | | | | 73/866.5 |
| 4,841,787 | A * | 6/1989 | Waterman | G01F 1/40 |
| | | | | 73/866.5 |
| 5,319,955 | A * | 6/1994 | Chastagner | G21C 17/044 |
| | | | | 376/256 |
| 5,441,071 | A * | 8/1995 | Doherty | G01N 1/2042 |
| | | | | 137/15.05 |
| 5,442,969 | A * | 8/1995 | Troutner | A61M 1/1609 |
| | | | | 73/863.02 |
| 5,460,054 | A * | 10/1995 | Tran | G01N 1/2035 |
| | | | | 73/864.33 |
| 5,580,444 | A * | 12/1996 | Burrows | B01D 61/12 |
| | | | | 210/257.2 |
| 5,587,926 | A * | 12/1996 | Chiu | G01F 23/24 |
| | | | | 702/179 |
| 5,627,330 | A * | 5/1997 | Preikschat | G01N 11/14 |
| | | | | 73/866.5 |
| 5,639,975 | A * | 6/1997 | Waterman | G01N 17/046 |
| | | | | 73/866.5 |
| 5,668,330 | A * | 9/1997 | Bartlett-Hooker | |
| | | | | G01N 35/1097 |
| | | | | 73/864.81 |
| 5,770,809 | A * | 6/1998 | Waterman | G01N 17/046 |
| | | | | 73/866.5 |
| 5,834,657 | A | 11/1998 | Clawson et al. | |
| 5,844,147 | A * | 12/1998 | Fiedler | G01N 1/40 |
| | | | | 73/863.21 |
| 5,844,148 | A | 12/1998 | Klein et al. | |
| 6,338,282 | B1 * | 1/2002 | Gilbert | G01N 1/14 |
| | | | | 73/864.34 |
| 7,472,615 | B2 * | 1/2009 | Mayeaux | G01N 17/046 |
| | | | | 73/866.5 |
| 7,505,857 | B2 * | 3/2009 | Howell | G01N 27/06 |
| | | | | 702/65 |
| 7,631,569 | B2 * | 12/2009 | Salo | G01B 5/0004 |
| | | | | 73/866.5 |
| 8,056,400 | B2 * | 11/2011 | Reintjes | G01N 1/2035 |
| | | | | 73/863.23 |
| 8,255,168 | B2 * | 8/2012 | Lutnick | G01N 33/22 |
| | | | | 702/182 |
| 8,342,003 | B2 * | 1/2013 | Burns | G01N 15/0205 |
| | | | | 73/23.35 |
| 8,342,043 | B2 * | 1/2013 | Stevens | G01N 1/14 |
| | | | | 73/863.61 |
| 8,434,372 | B2 * | 5/2013 | Fjerdingstad | G01N 1/2035 |
| | | | | 73/861.41 |
| 8,443,652 | B2 * | 5/2013 | Sahibzada | G01D 11/245 |
| | | | | 439/115 |
| 8,459,100 | B2 * | 6/2013 | Biberger | G01N 33/18 |
| | | | | 73/61.41 |
| 9,018,608 | B1 * | 4/2015 | Mayeaux | G01N 21/431 |
| | | | | 250/338.5 |
| 9,151,155 | B2 * | 10/2015 | Braaten | E21B 49/086 |
| 9,151,700 | B2 * | 10/2015 | Gransæther | G01N 1/2035 |
| 9,200,986 | B1 * | 12/2015 | Mayeaux | G01N 1/2035 |
| 9,410,871 | B1 * | 8/2016 | St. Amant, III | G01N 1/2247 |
| 9,476,867 | B2 * | 10/2016 | Lutnick | G06Q 99/00 |
| 9,635,442 | B1 * | 4/2017 | Chen | G01N 33/18 |
| 9,909,415 | B2 * | 3/2018 | Baker | E21B 47/10 |
| 9,970,899 | B2 * | 5/2018 | Sankaran | G01N 27/48 |
| 10,168,311 | B2 * | 1/2019 | Lutnick | F02P 5/145 |
| 10,190,980 | B2 * | 1/2019 | Rachman | G01N 21/51 |
| 10,288,595 | B2 * | 5/2019 | Anderson | G01N 33/1893 |
| 2005/0223829 | A1 | 10/2005 | Mayeaux | |
| 2014/0273052 | A1 | 9/2014 | Reddy et al. | |
| 2015/0285663 | A1 | 10/2015 | Schneider et al. | |
| 2020/0340968 | A1 * | 10/2020 | Zakinov | G01F 15/06 |

FOREIGN PATENT DOCUMENTS

| | | | | |
|---|---|---|---|---|
| CH | | 699850 | A2 | 5/2010 |
| CN | | 2210024 | Y | 10/1995 |
| CN | | 1882834 | A | 12/2006 |
| CN | | 101468822 | A | 7/2009 |
| CN | | 102553332 | A | 7/2012 |
| CN | | 102759608 | A | 10/2012 |
| CN | | 105417680 | A | 3/2016 |
| CN | | 205825497 | U | 12/2016 |
| CN | | 108267559 | A1 * | 7/2018 |
| EP | | 0616822 | A1 | 9/1994 |
| EP | | 2345886 | A1 | 7/2011 |
| FR | | 2708347 | A1 | 2/1995 |
| JP | | 2009115557 | A * | 5/2009 |
| JP | | 2010060395 | A * | 3/2010 |
| TW | | 201020019 | A | 6/2010 |
| WO | WO-03065032 | A2 * | 8/2003 | G01N 21/15 |
| WO | WO-2008148952 | A2 * | 12/2008 | C02F 1/006 |
| WO | WO-2010051842 | A1 * | 5/2010 | G01N 33/1893 |
| WO | | 2013172931 | A1 | 11/2013 |

OTHER PUBLICATIONS

ESPACENET Machine Translation of CN 108267559 A1 Which Originally Published on Jul. 10, 2018. (Year: 2018).*
China National Intellectual Property Administration, Office Action and Search Report Issued in Application No. 201880053416.6, dated Apr. 15, 2022, 26 pages.
ISA European Patent Office, International Search Report Issued in Application No. PCT/AT2018/060219, dated Jan. 15, 2019, WIPO, 2 pages.

* cited by examiner

_US 11,635,417 B2_

DEVICE FOR DETECTING THE QUALITY OF A LIQUID IN A SUPPLY PIPE

CROSS-REFERENCE TO RELATED APPLICATIONS

The present application is a U.S. National Phase of International Patent Application Serial No. PCT/AT2018/060219 entitled "DEVICE FOR DETECTING THE QUALITY OF A LIQUID IN A SUPPLY PIPE," filed on Sep. 20, 2018. International Patent Application Serial No. PCT/AT2018/060219 claims priority to Austrian Patent Application No. A 50814/2017 filed on Sep. 25, 2017. The entire contents of each of the above-referenced applications are hereby incorporated by reference for all purposes.

TECHNICAL FIELD

The invention relates to a device for detecting the quality of a liquid in a supply pipe, in particular for detecting the water quality in a water pipe, comprising a flow cell, which comprises an inlet opening, an outlet opening and at least one receiving device for the arrangement of at least one sensor.

The invention additionally relates to a combination of a supply pipe, in particular water pipe, with the above-mentioned device.

The invention lastly relates to a method for connecting the above-mentioned device to a supply pipe, in particular a water pipe.

BACKGROUND AND SUMMARY

Devices having at least one sensor for monitoring the quality of water are known.

The quality of liquids is often detected by taking samples of the liquid and analysing the samples externally with the aid of suitable measurement apparatuses. The removed liquid samples are disposed of after the analysis.

At some points of supply pipes there is no sewer connection provided, and therefore the removed liquid samples cannot be disposed of, or cannot be disposed of easily. The quality of liquids is therefore preferably detected also within the scope of a continuous flow process.

For example, CH 699 850 A2 discloses a sensor assembly and a method for monitoring the water quality in a water supply conduit. To this end, the sensor assembly comprises a flow cell having a plurality of sensors, which are used to detect various water quality features and to deliver current measurement data. The flow cell comprises a water inlet and a water outlet, which are connected, respectively, to an inflow pipe and an outflow pipe of the water supply conduit.

In the sensor assembly a one-way water flow path, which is accessible to the sensors, extends between the water inlet and the water outlet. The sensor assembly also comprises a communication unit for sending the current measurement data to a central controller.

The sensor assembly configured in this way can be mounted on the water supply conduit only laboriously or in time-consuming fashion and additionally hampers the execution of maintenance tasks that should be performed generally on the supply pipe at regular intervals.

The object of the present invention lies in creating a device and a method of the kind described at the outset which avoid or at least mitigate the disadvantages of the prior art. The device should be space-saving and economical, and it should be possible to mount the device easily on a supply pipe, in particular on a water supply conduit, also retrospectively. In addition, the device should facilitate the maintenance and the replacement of sensors associated with it and should also allow for regular maintenance works on the supply pipe.

The objects according to the invention are achieved by a device of above-described kind, in which the inlet opening and the outlet opening are provided on a base surface of the flow cell, which base surface is intended for connection to the supply pipe, the inlet opening of the flow cell is connected to an intake pipe, the free end of which is intended to be arranged in the supply pipe, which intake pipe is received displaceably in its longitudinal direction in the flow cell or is length-adjustable, and a liquid pump for a flow of the liquid in the supply pipe is connected to the intake pipe. The device for detecting the quality of a liquid in a supply pipe, in particular for detecting the water quality in a water pipe by means of at least one suitable sensor, therefore comprises a flow cell which is connectable to the sensor or the sensors. The flow cell comprises at least one receiving device for the connection of the at least one sensor to the flow cell. A receiving device for arranging or for mounting (or receiving) a sensor is preferably provided for each sensor to be connected to the flow cell. The flow cell additionally comprises an inlet opening and an outlet opening, which are provided on a base surface of the flow cell which base surface is intended for connection to the supply pipe. The base surface of the flow cell thus faces the supply pipe in an operating state of the device, in which the flow cell is arranged on the supply pipe. Liquid, of which the quality is to be detected, can be removed from the supply pipe through the inlet opening and introduced into the flow cell. Once the liquid has passed through the flow cell and has come into contact with the sensors as a result, it can exit again from the flow cell through the outlet opening and can flow back into the supply pipe. The inlet opening and the outlet opening are for this purpose arranged in alignment with a through-bore in a wall of the supply pipe in the operating state of the device. The flow of the liquid to be analysed through the flow cell is achieved or maintained using a liquid pump. The liquid pump expediently maintains a substantially constant flow of liquid in the flow cell, which has a favourable effect on the accuracy with which the quality of the liquid is detected. This can be justified in that the measurement accuracy of some sensors is dependent on the flow rate of the liquid in contact with the sensor. By comparison, in other devices without a liquid pump, in which the liquid flow through the flow cell establishes itself independently, additional measures must be taken in order to keep the liquid flow constant, or the measurement accuracy is lower in comparison to the device according to the invention. The liquid pump thus contributes to a high measurement accuracy. In order to be able to produce the flow cell with small dimensions, in particular with a small base surface, it is favourable if the inlet opening and the outlet opening are arranged side by side at the shortest possible distance from one another. Due to the preferably short distance between the inlet opening and the outlet opening, at least some of the liquid exiting from the outlet opening would be sucked back into the flow cell through the inlet opening if no further measures were provided. This applies in particular if the flow cell is mounted on the supply pipe by means of a tubular connection piece and is therefore arranged at a distance from the supply pipe, since within the connection piece there is practically no liquid flow brought about by the liquid in the supply pipe. Some of the liquid already analysed would therefore be measured again. In order to prevent this, i.e. in order to always conduct new liquid from the supply pipe into the flow cell, the inlet opening of the flow cell is connected to an intake pipe. The intake pipe is intended to be arranged in the supply pipe, i.e. inserted into the supply pipe, via its free end opposite the flow cell. The intake pipe therefore extends from the flow cell or from its base surface in the direction of the supply pipe, when the flow cell is arranged on the supply pipe. The distance between the position at which the liquid is removed from the supply pipe and the outlet opening is therefore increased by means of the intake pipe, and a circulation of liquid discharged from the flow cell back into the flow cell is avoided. In order to ensure a suitable positioning of the free end of the intake pipe, the intake pipe is received displaceably or adjustably in its longitudinal direction in the flow cell, or is length-adjustable. The free end of the intake pipe may thus be displaced with respect to the flow cell, in particular with respect to the base surface of the flow cell. The intake pipe is expediently connected in liquid-tight fashion to the inlet opening and is in any case connected to the liquid pump in order to be able to conduct liquid from the supply pipe through the intake pipe and through the flow cell. If the intake pipe is length-adjustable, it may comprise, for example, at least two parts displaceable telescopically relative to one another. With the described device the quality of the liquid can be detected in situ, without the need to take samples and dispose of them after the analysis. The device may thus also be installed at points of the supply pipe where there is no drain or sewer connection provided. In addition, the device may provide a space-saving design on account of the small base surface. Furthermore, the device can be produced economically, since the intake pipe and the liquid pump itself incur only low costs.

If reference is made within the scope of the description to the position specifications "upper" or "lower" on the flow cell, this shall be understood on the assumption that the base surface is located at the bottom on the flow cell. This does not rule out that the flow cell could be connected to the supply pipe, ready for operation, above or laterally of the supply pipe.

In contrast to known devices which provide a first pipe for connection to an inlet opening of the flow cell and a second pipe for connection to an outlet opening of the flow cell, the device according to the invention comprises a single connection point for connection of the flow cell to the supply pipe. Thus, in contrast to the known device, only a single opening must be formed in the supply pipe in order to produce a connection between the flow cell and the supply pipe. The resultant saving in time for the mounting of the device on the supply pipe leads to a reduction in the effort and cost. In addition, the device with a single connection point leads to a saving of material costs. Since, for connection to the device, only a single opening needs to be formed in the supply pipe, the mounting location of the device is subject to fewer restrictions. In addition, the device as a whole covers a shorter longitudinal portion on the supply pipe, whereby the mounting costs may be further reduced. It is particularly favourable that the device may be mounted quickly and easily, retrospectively on an existing pressurised supply pipe.

In accordance with a preferred embodiment of the invention it may be provided that, in an operating state of the flow cell connected to the supply pipe, the free end of the intake pipe extends as far as a wall of the supply pipe. The intake pipe, in the operating state of the flow cell, is thus designed and arranged to extend with its free end as far as a wall of the supply pipe, in particular as far as an inner face of the wall of the supply pipe. It is thus ensured that liquid removed directly from the supply pipe is pumped through the intake pipe and through the flow cell, which liquid comprises portions of the liquid discharged from the flow cell at most only to a small extent. If the intake pipe is not inside the supply pipe, i.e. does not extend beyond the inner wall of the supply pipe, maintenance works can be performed in the supply pipe at any time, without having to change the position of the intake pipe.

For a compact design of the flow cell it is favourable if the liquid pump is attached to the flow cell. For example, the liquid pump may be mounted detachably on the base surface of the flow cell. In this way, the liquid pump can be removed from the flow cell as necessary, for example in order to be replaced. Since only a small amount of energy is necessary to convey the liquid through the flow cell, the liquid pump may be designed for a power of approximately 1 W, and for example may be battery-operated.

In order to avoid an escape of liquid from the supply pipe or from the flow cell, at least one closure means for shutting off the flow of liquid in the supply pipe in the direction to the flow cell or away from the flow cell may be provided. The liquid flow branched off from the supply pipe and flowing through the flow cell may therefore be stopped by means of the closure means, without having to shut off the supply pipe. The closure means may be provided in the flow cell itself or particularly preferably on the supply pipe. If the closure means is arranged on the supply pipe, in order to seal off the opening in the supply pipe as necessary, which opening is intended for insertion of the intake pipe, the entire device according to the invention may be removed from the supply pipe, without having to shut off the supply pipe. The closure means thus makes it possible for the sensors in contact with the branched-off liquid flow to be removed from the flow cell once the closure means has been closed, without an undesirable significant escape of liquid from the flow cell. The closure means for example may be formed by a sliding body which is received between two seals, is manually actuated, and in particular is movable transverse to the flow direction.

It is particularly favourable if an adjustment means for the intake pipe is provided for adjusting the intake pipe in the longitudinal direction of the intake pipe between a retracted position remote from the supply pipe in the operating state of the flow cell and a deployed position extended to the supply pipe in the operating state of the flow cell. The adjustment means facilitates the mounting of the device on the supply pipe, since the distance of the free end of the intake pipe from the base surface of the flow cell can be changed using the adjustment means, also following the establishment of a connection between the device and the supply pipe. In particular, the free end of the intake pipe can be extended as far as the inner wall of the supply pipe. However, it is not ruled out that the free end of the intake pipe can be extended until it is reaching into the supply pipe. For the adjustment of the intake pipe, it may be pulled out of or inserted into the supply pipe along the longitudinal extent of the intake pipe, for example by means of an actuation rod connected to the intake pipe, which actuation rod protrudes from the flow cell in order to be actuated by a user. In accordance with another example, the intake pipe may comprise a thread portion along its longitudinal extent, which thread portion engages in a corresponding thread portion in the flow cell or in a support body connected to the flow cell. A hand grip is expediently provided in order to adjust the intake pipe. It is particularly advantageous if the intake pipe is received slidably in a support body, which is designed to be arranged detachably in the flow cell.

In order to avoid contaminations of the flow cell or sensors, a sediment filter may be provided in the flow cell, before the at least one receiving device in the flow direction of the liquid, or in the intake pipe. The intervals between maintenance of the flow cell may thus also be increased. The sediment filter is expediently fastened detachably, so as to be able to clean or replace it as necessary.

It is favourable if the liquid pump is designed to pump the liquid in opposite directions or if a rerouting means is provided in order to reverse the flow direction of the liquid through the sediment filter. The liquid pump may therefore be switchable in order to reverse the rotation direction. The rerouting means can be provided alternatively to a liquid pump that is designed to pump the liquid in opposite directions. The rerouting means preferably comprises pipelines and a directional valve for rerouting the liquid through the pipelines. The sediment filter may thus be cleaned by reversing the flow direction of the liquid through the sediment filter.

In accordance with a further embodiment at least one sensor may be arranged in the flow cell, which sensor may be formed by a flow sensor, a pressure sensor, a spectrometer probe, an ion-selective probe, an electrochemical sensor, or an optical sensor. Of course, a plurality of sensors, in particular a combination of the above-mentioned sensors, may be arranged in the flow cell. In particular, at least one sensor may be arranged in the flow cell, which sensor detects the conductivity of the liquid or of water, a content of free chlorine, a content of total chlorine, a pH value, a turbidity of the liquid, a TOC (total organic carbon) value and/or the colour of the liquid or water.

If at least one receiving device is designed to screw or plug at least one sensor into the flow cell, the sensor can be easily and quickly reliably arranged in the receiving device and removed again therefrom. The screw connection or plug-in connection of the receiving device and of the sensor provided for this purpose is preferably liquid-tight. In particular, a screw connection or plug-in connection can be provided for each individual sensor to be arranged in the flow cell. Those receiving devices in which there is no sensor arranged, regardless of the type of connection to the sensor, are preferably closed liquid-tight by a closure element. In the case of the screw connection/plug-in connection, the closure element may be a lid screwable/pluggable with/in the receiving device. In addition, a receiving device for arranging, in particular screwing or plugging, the intake pipe or a support body surrounding the intake pipe in the flow cell can be provided.

For a stable design of the device according to the invention, the flow cell and/or the intake pipe may be formed at least in part of metal and/or plastic, preferably polyoxymethylene. In particular, the flow cell may be formed from stainless steel in a lower region adjoining the base surface, and may be formed from polyoxymethylene, which is approved for drinking water, in an upper region comprising the receiving device. For reasons of hygiene, an intake pipe is preferably formed from stainless steel.

So as not to compromise the detection of the quality of the liquid in the supply pipe due to air sucked in from the supply pipe, the flow cell may comprise, or may be connected to, a ventilation device, in particular a ventilation valve. The ventilation device is expediently designed for automatic ventilation and is arranged in an upper region of the flow cell.

If the flow cell comprises a removal device, preferably a ball valve, for taking a liquid sample, the quality of the liquid sample may be detected in an apparatus arranged externally of the device according to the invention. The removal device thus enables easy access to the liquid in the supply pipe and, possibly, the detection of features of the liquid which cannot be detected by the sensors in the flow cell. The removal device may be designed for manual or automatic actuation.

The object according to the invention is also achieved by a combination of a supply pipe, in particular water pipe, with the previously described device, wherein the intake pipe of the device protrudes into the supply pipe through a single opening in a wall of the supply pipe. The combination may additionally comprise a preferably tubular connection piece between the flow cell and the supply pipe, by means of which connection piece the flow cell is connected to the supply pipe. Reference should be made to the above description in respect of the advantages that result from the single opening in the supply pipe.

The object according to the invention is also achieved by a method of the described kind, in which a through-bore is made in a wall of the supply pipe, and the closure means and then the flow cell are fixed to the wall, in alignment with the through-bore. In particular, the free end of the intake pipe and the outlet opening of the flow cell are arranged in alignment with the through-bore. The arrangement of the flow cell in alignment with the through-bore ensures the liquid connection, necessary for the operation of the device, between the supply pipe, the free end of the intake pipe and the outlet opening of the flow cell. Reference should also be made to the above description of the device in respect of the advantages attainable by this method. The method for connecting the above-described device to a supply pipe, in particular a water pipe, can be carried out particularly easily, since only a single bore needs to be made in the wall of the supply pipe.

In accordance with a preferred embodiment of the method, the intake pipe may be deployed from the flow cell as far as the supply pipe by way of the adjustment means, preferably following the fixing of the flow cell to the supply pipe. If the adjustment means for the intake pipe is provided, the position of the free end of the intake pipe can be adjusted relative to the supply pipe following the fixing of the flow cell to the supply pipe. If there is no adjustment means provided, the position of the free end of the intake pipe can be determined by the suitable selection of the length of the intake pipe.

If at least one closure means for shutting off the liquid flow branched off from the supply pipe in the direction towards the flow cell or away from the flow cell is provided, the closure means may be opened before the intake pipe is deployed from the flow cell fixed to the supply pipe. In this way, by closing the closure means, liquid is prevented from exiting undesirably from the connection points prior to the flow cell being connected to the supply pipe or prior to the sensor being connected to the receiving device. If the connections of the flow cell to the supply pipe and the connection of the sensor to the receiving device have been established, the flow path through the flow cell for the liquid that has been branched off from the supply pipe and is to be analysed is released by opening the closure means.

BRIEF DESCRIPTION OF THE FIGURES

The invention will be explained hereinafter in greater detail on the basis of preferred, non-limiting exemplary embodiments with reference to the drawings, in which:

FIG. 3b shows the device from FIG. 1 in a state connected to a supply pipe, in a perspective view from an opposite direction as compared to FIG. 3a;

DETAILED DESCRIPTION

Figure 1:
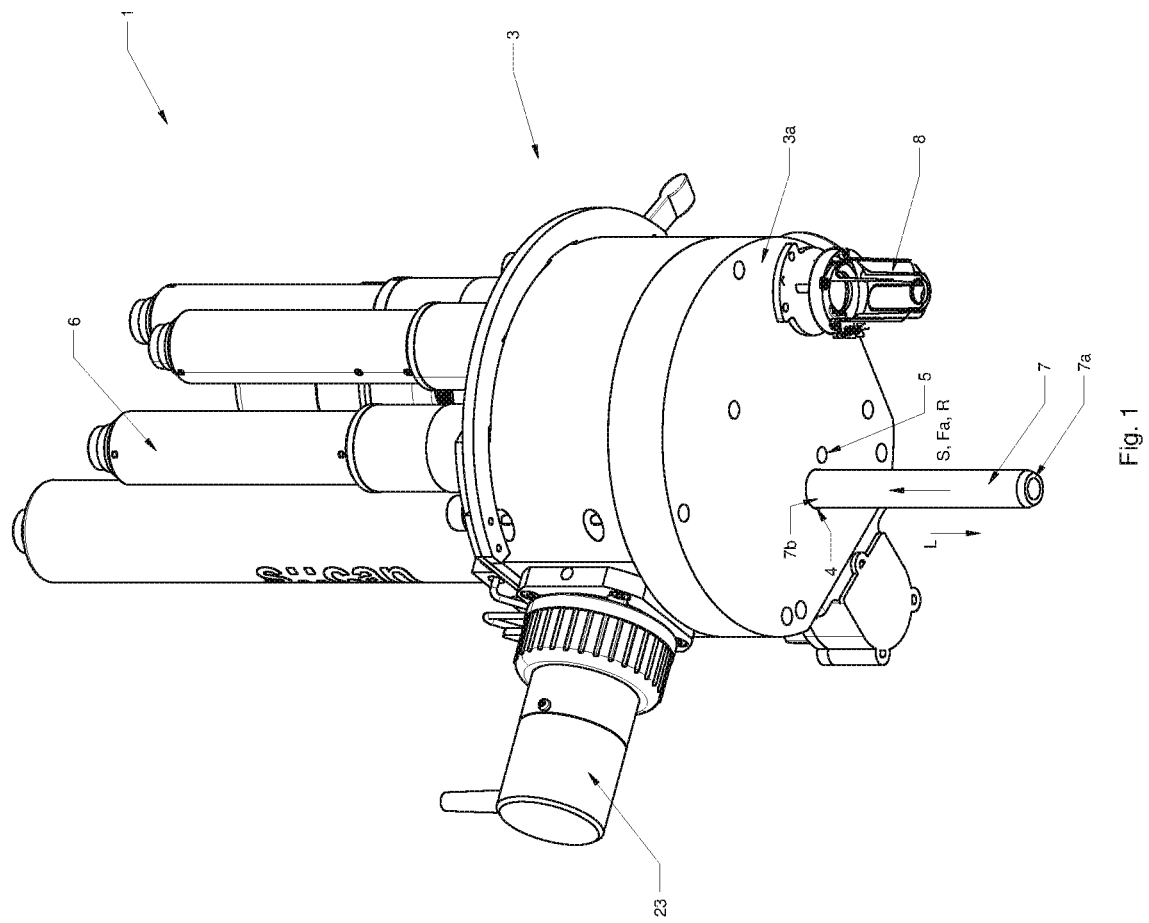
FIG. 1 shows a device according to the invention with a flow cell and an intake pipe, in a perspective view.

FIG. 1 shows the device 1 for detecting the quality of a liquid F in a supply pipe 2 (not shown in FIG. 1), which comprises a flow cell 3 and an intake pipe 7 connected or connectable thereto. On a base surface 3a of the flow cell 3, which base surface 3a faces the supply pipe 2 when the flow cell 3 is connected to the supply pipe 2 in the operating state of the device 1, the flow cell 3 comprises an inlet opening 4 and an outlet opening 5. The inlet opening 4 and the outlet opening 5 are arranged as closely as possible to one another so as to be able to be arranged jointly over a single opening 15 in the supply pipe 2. The inlet opening 4 is connected to the intake pipe 7, in particular to an end 7b of the intake pipe 7, in order to be able to feed liquid F, in particular water, from the supply pipe 2, through the intake pipe 7, and through the inlet opening 4 of the flow cell 3, and divert said liquid out from the flow cell 3, back into the supply pipe 2 through the outlet opening 5. The flow cell 3 comprises a liquid channel (not shown) between the inlet opening 4 and the outlet opening 5, along which liquid channel the branched-off liquid Fa flows over sensors 6 arranged therein. In order to detect the quality of the liquid Fa (FIGS. 3a, 3b) which is branched off from the supply pipe 2, in particular from a water pipe, by means of the intake pipe 7, the flow cell 3 comprises at least one receiving device 10 for the arrangement of at least one sensor 6. In accordance with the shown exemplary embodiment, four sensors 6 are connected to the flow cell 3, wherein each sensor 6 is preferably assigned a separate receiving device 10. The receiving device 10 may comprise a thread or plug system 18 (FIG. 3a) for introducing, in particular screwing or plugging, the sensor 6 into the flow cell 3. The sensor 6 for this purpose comprises a corresponding thread or plug system. Of course, the flow cell 3 may be designed to receive any number of sensors 6. The number of sensors 6 connected to the flow cell 3 may be lower than the number of receiving devices 10, wherein the free receiving devices 10 in this case may be closed off in liquid-tight fashion by a closure (not shown).

FIG. 1 additionally shows a liquid pump 8 for pumping a flow S, that has been branched off from the liquid F in the supply pipe 2, through the intake pipe 7, the inlet opening 4, the flow cell 3, and through the outlet opening 5. The liquid pump 8 is to this end connected to the intake pipe 7, the inlet opening 4, the liquid channel (not shown) in the flow cell 3, in which liquid channel the sensors 6 are arranged, and the outlet opening 5. The liquid pump 8, in the example shown in FIG. 1, is mounted on the base surface 3a of the flow cell 3. In FIG. 1 a cleaning device 23 for cleaning the sensors 6 arranged in the flow cell 3 is also visible.

Figure 3B:
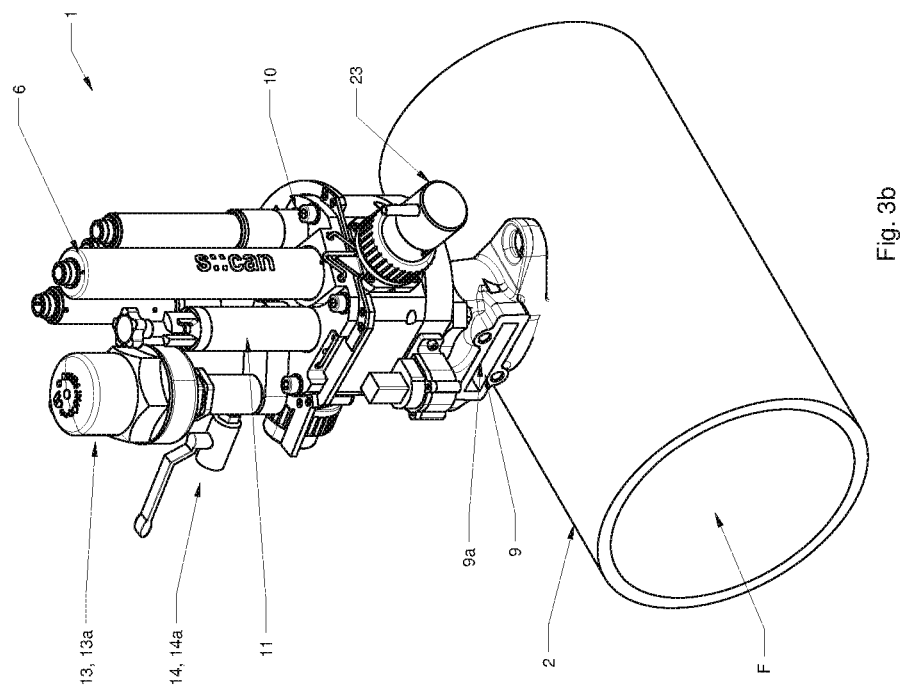
Figure 3A:
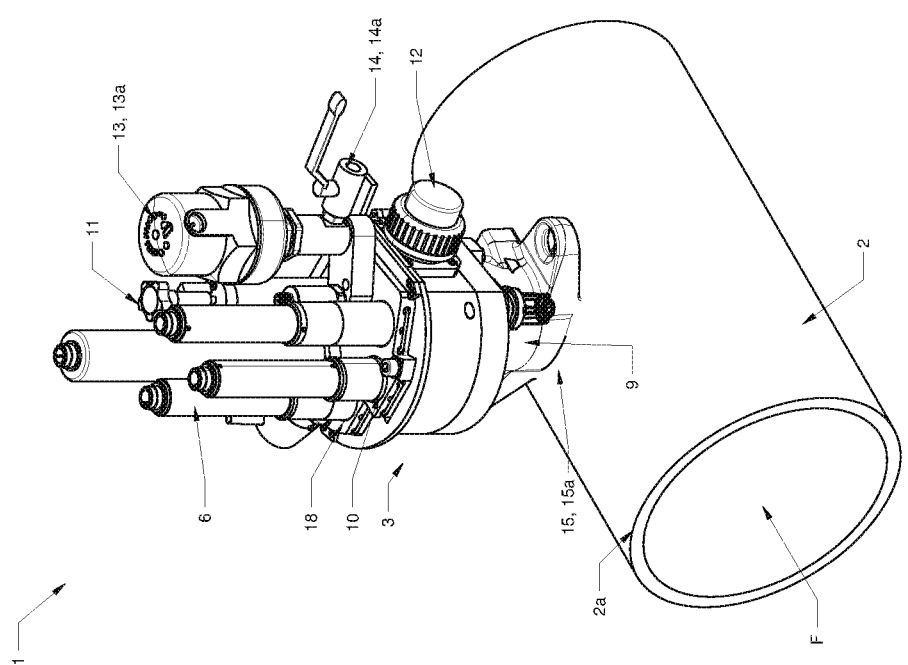
FIG. 3a shows the device from FIG. 1 in a state connected to a supply pipe, in a perspective view.

As can be better seen in FIGS. 3a and 3b, a sediment filter 12 may also be provided and may be arranged in the flow cell 3 before the at least one receiving device 10 in the flow direction of the branched-off liquid Fa. Alternatively, the sediment filter 12 may be arranged in the intake pipe 7. The sediment filter 12 filters out particles from the branched-off liquid Fa, which particles could falsify the measurement of the sensors 6 or could shorten the maintenance interval for the sensors 6 or for the flow cell 3.

A ventilation device 13, which in particular may be a ventilation valve 13a, can also be seen in FIGS. 3a and 3b. Air which has been sucked into the flow cell 3 from the supply pipe 2 by means of the liquid pump 8 is diverted into the surrounding environment via the ventilation device 13. In order to be able to take liquid samples, the flow cell 3 may comprise a removal device 14, for example a manually actuatable ball valve 14a.

As can also be seen in FIGS. 3a and 3b, an adjustment means 11 for the intake pipe 7 may be provided in the flow cell 3. The adjustment means 11 is used to adjust the intake pipe 7, in its longitudinal direction L, between a retracted position and a deployed position. The adjustment means 11 may be received detachably in the receiving device 10, similarly to the sensors 6.

Figure 2C:
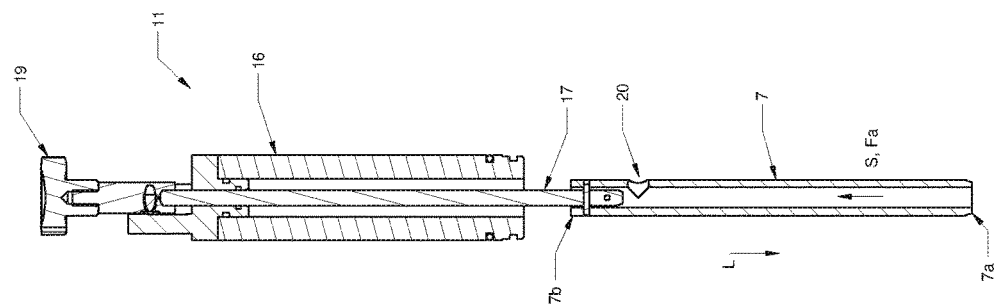
FIG. 2c shows the intake pipe of the device from FIG. 1 in a deployed state, in a sectional view.
Figure 2B:
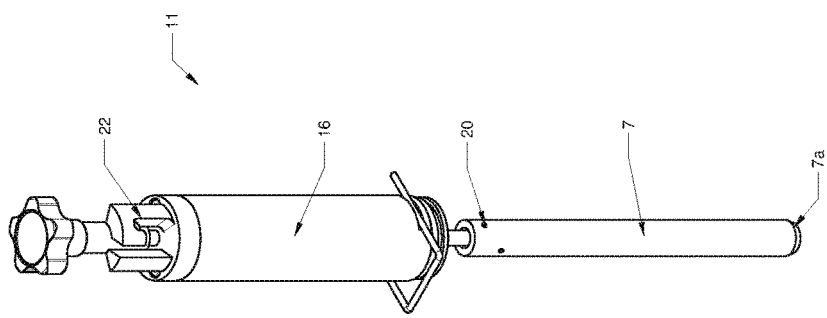
FIG. 2b shows the intake pipe of the device from FIG. 1 in a deployed state, in a perspective view.
Figure 2A:
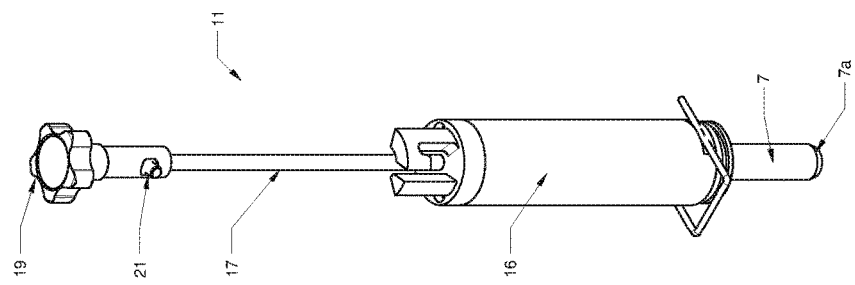
FIG. 2a shows the intake pipe of the device from FIG. 1 in a retracted state, in a perspective view.

FIGS. 2a to 2c show the adjustment means 11 in greater detail. The adjustment means 11 may comprise a guide pipe 16, in which an actuation rod 17 is received displaceably and is connected to the intake pipe 7. By displacement of the actuation rod 17 in the longitudinal direction L of the intake pipe 7, the position of the intake pipe 7 may thus be adjusted. Here, FIG. 2a shows the intake pipe 7 in a position retracted into the guide pipe 16 or into the flow cell 3, in which position the intake pipe 7 is distanced from the supply pipe 2 in the operating state of the flow cell 3. By contrast, FIG. 2b shows the intake pipe 7 in a position deployed from the guide pipe 16 or from the flow cell 3, in which position the intake pipe is extended to the supply pipe 2 in the operating state of the flow cell 3.

In order to deliver the flow S of the branched-off liquid Fa from the intake pipe 7 into the flow cell 3, in particular into the liquid channel (not shown), along which the branched-off liquid flow S flows over the sensors 6 arranged therein, the intake pipe 7 comprises openings 20. In the retracted state of the intake pipe 7, the openings 20 are sealed off expediently by the inner wall of the guide pipe 16. The actuation rod 17 is expediently provided with a hand grip 19 that can be easily grasped by a user. In addition, a securing pin 21 may be provided on the actuation rod 17, and a detent element 22 may be provided on the guide pipe 16 for reciprocal engagement. For example, the securing pin 21 may be engaged with the detent element 22 by turning the hand grip 19, whereby an unintentional removal of the intake pipe 7 from the supply pipe 2, i.e. a retraction of the intake pipe 7 into the guide pipe 16 or into the flow cell 3, is prevented.

FIGS. 3a and 3b show a combination of the supply pipe 2, in particular water pipe, with the device 1. In particular, the device 1 is shown in a state mounted on the supply pipe 2, as viewed from two opposite directions. Here, it can be seen that a closure means 9 is provided between the device 1, in particular the flow cell 3, and the supply pipe 2. The closure means 9 is used to shut off the flow S of the liquid F in the supply pipe 2 in the direction towards the flow cell 3 or away from the flow cell 3. To this end, for example a plate member insertable into an opening 9a of the closure means 9 may close the liquid connection between the supply pipe 2 and the flow cell 3. The closure means 9, which is substantially tubular in the shown example, is also used as a connection piece between the flow cell 3 and the supply pipe 2.

Figure 4B:
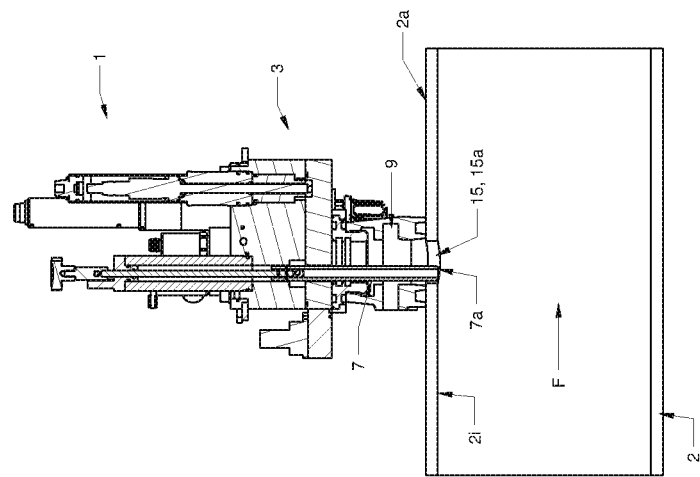
FIG. 4b shows the device from FIG. 1 in a state connected to a supply pipe, with deployed intake pipe and with an opened closure means, in a sectional view transverse to the longitudinal direction of the supply pipe.
Figure 4A:
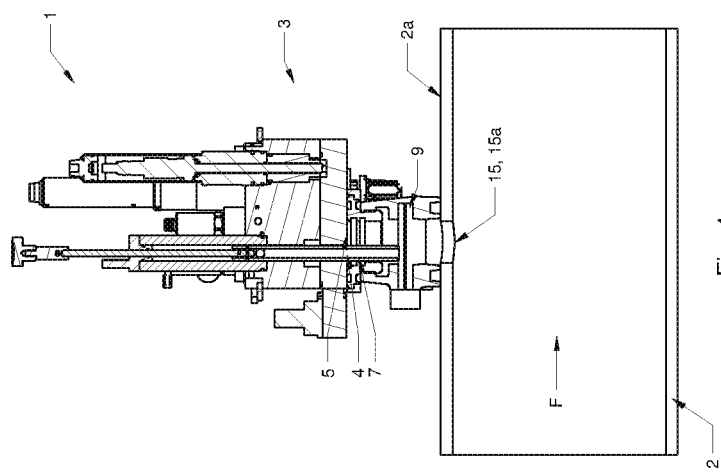
FIG. 4a shows the device from FIG. 1 in a state connected to a supply pipe, with retracted intake pipe and with a closed closure means, in a sectional view transverse to the longitudinal direction of the supply pipe.

FIGS. 4a and 4b show the combination of the supply pipe 2, in particular water pipe, with the device 1 in a sectional view. It is clearly visible that the flow cell 3, in particular the inlet opening 4 and the intake pipe 7, and also the outlet opening 5, are arranged above a single through-bore 15a in a wall 2a of the supply pipe 2.

In FIG. 4 the device 1 is shown in an operating state connected to the supply pipe 2, wherein the intake pipe 7 is retracted and the closure means 9 is closed. For example, the sensors 6, when the closure means 9 is closed, may thus be removed or replaced, without an undesirable escape of liquid from the flow cell 3.

In FIG. 4b the device 1 is shown in an operating state connected to the supply pipe 2, wherein the intake pipe 7 is deployed and the closure means 9 is open. The lower or free end 7a of the intake pipe 7 opposite the flow cell 3 protrudes through the single opening 15 or through-bore 15a in the wall 2a of the supply pipe 2, into the supply pipe 2. In particular, the free end 7a of the intake pipe 7 extends as far as the inner wall 2i of the supply pipe 2.

Figure 5:
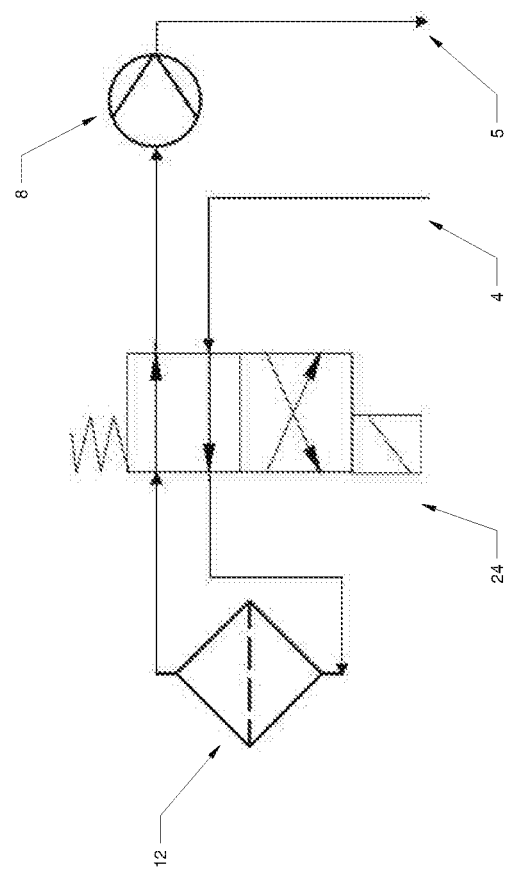
FIG. 5 shows a schematically illustrated rerouting means for reversing the flow direction of the liquid through a sediment filter in the device from FIG. 1.

FIG. 5 shows schematically a rerouting means 24 of the device 1, which rerouting means 24 is designed to reverse the flow direction of the branched-off liquid Fa through the sediment filter 12. In the example shown in FIG. 5 the rerouting means 24 is a directional valve or comprises such a valve. The rerouting means 24 or the directional valve conducts the branched-off liquid flow S through the sediment filter 12 in one of two opposite directions selectively. In this way, the sediment filter 12 may be cleaned as necessary by reversing the flow direction of the branched-off liquid Fa through the sediment filter 12. In the example shown in FIG. 5, the liquid pump 8 is expediently designed to pump the liquid F, Fa in a single direction, i.e. from the inlet opening 4 to the outlet opening 5 of the flow cell 3.

The invention claimed is:

1. A device for detecting the quality of a liquid in a supply pipe, comprising:
a flow cell which comprises an inlet opening, an outlet opening, and at least one receiving device for the arrangement of at least one sensor, the inlet opening and the outlet opening provided on a base surface of the flow cell which base surface is intended for connection to the supply pipe, the inlet opening of the flow cell is connected to an intake pipe, a free end of the intake pipe configured for arrangement in the supply pipe, an adjustment means for the intake pipe is provided in the flow cell and said intake pipe being received displaceably in its longitudinal direction in the flow cell by the adjustment means or is configured to be adjustable in its length by the adjustment means, and a liquid pump for a flow of the liquid in the supply pipe is connected to the intake pipe.

2. The device according to claim 1, wherein the free end of the intake pipe extends as far as a wall of the supply pipe in an operating state of the flow cell connected to the supply pipe.

3. The device according to claim 1, wherein the liquid pump is mounted on the flow cell.

4. The device according to claim 1, wherein at least one closure means is provided for shutting off the flow of the liquid in the supply pipe in a direction towards the flow cell or away from the flow cell.

5. The device according to claim 1, wherein the adjustment means for the intake pipe is provided for adjusting the intake pipe in the longitudinal direction of the intake pipe between a retracted position distanced from the supply pipe in the operating state of the flow cell and a deployed position extended to the supply pipe in the operating state of the flow cell.

6. The device according to claim 1, wherein at least one sensor is arranged in the flow cell and is formed by a flow sensor, a pressure sensor, a spectrometer probe, an ion-selective probe, an electrochemical sensor, or an optical sensor.

7. The device according to claim 1, wherein at least one receiving device is configured to screw or plug at least one sensor into the flow cell.

8. The device according to claim 1, wherein the flow cell and/or the intake pipe is formed at least in part of metal and/or plastic.

9. The device according to claim 1, wherein the flow cell comprises or is connected to a ventilation device.

10. The device according to claim 1, wherein the flow cell comprises a removal device for taking a liquid sample.

11. The device according to claim 1, wherein when the device is coupled to the supply pipe the intake pipe of the device protrudes through a single opening in a wall of the supply pipe into the supply pipe.

12. The device according to claim 1, wherein the device is coupled to a water pipe and is configured to detect water quality in the water pipe.

13. The device according to claim 1, wherein the flow cell and/or the intake pipe is formed at least in part of polyoxymethylene.

14. The device according to claim 1, wherein the flow cell comprises or is connected to a ventilation valve.

15. The device according to claim 1, wherein the flow cell comprises a ball valve for taking a liquid sample.

16. The device according to claim 1, wherein a sediment filter is provided in the flow cell before the at least one receiving device in a flow direction of the liquid, or is provided in the intake pipe.

17. The device according to claim 16, wherein the liquid pump is configured to pump the liquid in opposite directions, or a rerouting means for reversing the flow direction of the liquid through the sediment filter is provided.

18. A method for connecting a device to a supply pipe, comprising:
forming a through-bore in a wall of the supply pipe; fixing a closure means and then a flow cell of the device to the wall, in alignment with the through-bore, the flow cell including an inlet opening, an outlet opening, and at least one receiving device for the arrangement of at least one sensor, the inlet opening and the outlet opening provided on a base surface of the flow cell configured for connection to the supply pipe, the inlet opening of the flow cell connected to an intake pipe, a free end of the intake pipe configured for arrangement in the supply pipe, an adjustment means for the intake pipe is provided in the flow cell and said intake pipe being received displaceably in its longitudinal direction in the flow cell by the adjustment means or is configured to be adjustable in its length by the adjustment means, and the device includes a liquid pump connected to the intake pipe for a flow of the liquid in the supply pipe, the closure means provided for shutting off the flow of the liquid in the supply pipe in a direction towards the flow cell or away from the flow cell.

19. The method according to claim 18, wherein the intake pipe is deployed from the flow cell via the adjustment means, as far as the supply pipe.

20. The method according to claim 19, wherein the closure means is opened before the intake pipe is deployed from the flow cell.

* * * * *